United States Patent
Shin et al.

(10) Patent No.: US 9,316,906 B2
(45) Date of Patent: Apr. 19, 2016

(54) FLUORENE OXIME ESTER COMPOUND, PHOTOPOLYMERIZATION INITIATOR AND PHOTORESIST COMPOSITION CONTAINING THE SAME

(71) Applicants: KOREA RESEARCH INSTITUTE OF CHEMICAL TECHNOLOGY, Daejeon (KR); SAMYANG CORPORATION, Seoul (KR)

(72) Inventors: Seung Rim Shin, Daejeon (KR); Kun Jun, Daejeon (KR); Jong Il Shin, Daejeon (KR); Soo Youl Park, Daejeon (KR); Kyoung Lyong An, Daejeon (KR); Sang Oh Lee, Mokpo-si (KR); Bong Seok Moon, Daejeon (KR); Chunrim Oh, Seoul (KR); Anam Choi, Jinju-si (KR); In-Young So, Chungcheongnam-do (KR)

(73) Assignees: KOREA RESEARCH INSTITUTE OF CHEMICAL TECHNOLOGY, Daejeon (KR); SAMYANG CORPORATION, Seoul (KR)

( * ) Notice: Subject to any disclaimer, the term of this patent is extended or adjusted under 35 U.S.C. 154(b) by 0 days.

(21) Appl. No.: 14/398,565

(22) PCT Filed: May 3, 2013

(86) PCT No.: PCT/KR2013/003847
§ 371 (c)(1),
(2) Date: Nov. 3, 2014

(87) PCT Pub. No.: WO2013/165207
PCT Pub. Date: Nov. 7, 2013

(65) Prior Publication Data
US 2015/0111152 A1    Apr. 23, 2015

(30) Foreign Application Priority Data

May 3, 2012 (KR) .......................... 10-2012-0047095
May 3, 2013 (KR) .......................... 10-2013-0049811

(51) Int. Cl.

| G03F 7/004 | (2006.01) |
|---|---|
| C07C 251/66 | (2006.01) |
| C07C 251/68 | (2006.01) |
| G03F 7/027 | (2006.01) |
| G03F 7/00 | (2006.01) |
| G03F 7/031 | (2006.01) |
| G03F 7/105 | (2006.01) |

(52) U.S. Cl.
CPC .............. *G03F 7/027* (2013.01); *C07C 251/66* (2013.01); *C07C 251/68* (2013.01); *G03F 7/0007* (2013.01); *G03F 7/031* (2013.01); *G03F 7/105* (2013.01); *C07C 2103/18* (2013.01)

(58) Field of Classification Search
None
See application file for complete search history.

(56) References Cited

U.S. PATENT DOCUMENTS

| 8,133,656 B2 | 3/2012 | Sawamoto et al. |
|---|---|---|
| 2001/0012596 A1 | 8/2001 | Kunimoto et al. |
| 2009/0087759 A1 | 4/2009 | Matsumoto et al. |

FOREIGN PATENT DOCUMENTS

EP    2072500 B1    9/2012

OTHER PUBLICATIONS

International Search Report Appln. No. PCT/KR2013/003847; Issued Jul. 30, 2013.

*Primary Examiner* — Cynthia H Kelly
*Assistant Examiner* — Alyssa L Cepluch
(74) *Attorney, Agent, or Firm* — Ladas & Parry LLP

(57) ABSTRACT

Provided are a novel fluorene oxime ester compound, and a photopolymerization initiator and a photoresist composition containing the same.

8 Claims, No Drawings

FLUORENE OXIME ESTER COMPOUND, PHOTOPOLYMERIZATION INITIATOR AND PHOTORESIST COMPOSITION CONTAINING THE SAME

TECHNICAL FIELD

The present invention relates to a novel fluorene oxime ester compound and a photopolymerization initiator and a photoresist composition containing the same.

BACKGROUND ART

As a general example of a photopolymerization initiator used in a photoresist composition, there have been known various types such as acetophenone derivatives, benzophenone derivatives, triazine derivatives, biimidazole derivatives, acylphosphine oxide derivatives, oxime ester derivatives, and the like. Among them, the oxime ester derivatives have advantages in that they exhibit almost colorless after absorbing ultraviolet, and have high radical generation efficiency, and excellent compatibility with raw materials of a photoresist composition and stability. However, the initially developed oxime derivatives have low photoinitiation efficiency and particularly low sensitivity at the time of performing a pattern exposure process, such that an exposure dose should be increased, thereby decreasing productivity.

Therefore, through the development of a photopolymerization initiator having excellent photosensitivity, sufficient sensitivity may be implemented even by a small amount of photopolymerization initiator, such that a cost may be decreased, and an exposure dose may be decreased due to excellent sensitivity, thereby making it possible to increase the productivity.

Various oxime ester derivatives that may be used as a photoinitiator in the photoresist composition and represented by the following Chemical Formula 2 have been already known.

[Chemical Formula 2]

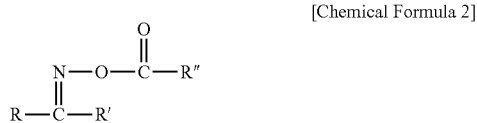

In the case of a photoinitiator having an oxime ester group, it is easy to synthesize various photoinitiators capable of adjusting an absorption region of the photoinitiator by introducing appropriate substituents at R, R' and R" of the compound.

The oxime ester compound may provide an excellent achievement in polymerization and curing a polymerizable compound having an unsaturated bond by irradiated with light of from 365 to 435 nm on a photoresist composition, thus the utility of the oxime ester compound has been extended into a black matrix, a color filter, a column spacer, a flexible insulator film, a photoresist composition for overcoat, or the like.

Therefore, a novel photoinitiator capable of having high sensitivity to light source of long wavelength of from 365 to 435 nm, or the like, and excellent photopolymerization reactivity, being easily manufactured, being easily handled due to high thermal stability and storage stability, and satisfying industrial requirements such as a satisfactory solubility in a solvent (propylene glycol monomethyl ether acetate (PG-MEA)), or the like, to thereby be appropriate for various purposes has been continuously demanded.

Recently, research into a photoresist composition used in a thin film display such as a liquid crystal device, or an organic light emitting diode (OLED), and the like, and more particularly, research into a photoresist composition containing a high sensitivity photoinitiator capable of being developed by an alkaline developer solution to form a pattern as an organic insulator film of the liquid crystal device such as a thin film transistor liquid crystal display (TFT-LCD), a column spacer, an UV overcoat, red, green, blue (R.G.B) color resist, a black matrix, and the like, has been mainly conducted.

Generally, as a resist composition used in order to form a pattern, a photoresist composition containing a binder resin, a multi-functional monomer having an ethylenically unsaturated bond, and a photoinitiator has been preferably used.

However, in the case of using the existing photoinitiator to form a pattern, sensitivity is low during an exposure process for forming the pattern, such that a usage amount of the photoinitiator or an exposure dose should be increased. Therefore, there are problems in that a mask may be contaminated during the exposure process, an output may be decreased due to by-products generated after the photoinitiator is decomposed by hot crosslinking, a productivity may be decreased due to an increase in an exposure process time according to the increase in the exposure dose, and thus an effort for solving these problems has been conducted.

DISCLOSURE

Technical Problem

An object of the present invention is to provide a novel fluorene oxime ester compound, a photopolymerization initiator containing the same, and a photoresist composition capable of having higher sensitivity while decreasing a usage of the photopolymerization initiator containing the novel fluorene oxime ester compound.

Technical Solution

In one general aspect, there are provided a compound represented by the following Chemical Formula 1 and a photopolymerization initiator and a photoresist composition containing the compound.

[Chemical Formula 1]

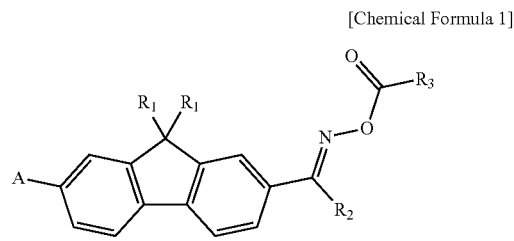

In Chemical Formula 1,
$R_1$ to $R_3$ each are independently hydrogen, halogen, $(C_1-C_{20})$alkyl, $(C_6-C_{20})$aryl, $(C_1-C_{20})$alkoxy, $(C_1-C_{20})$aryl$(C_1-C_{20})$alkyl, hydroxy $(C_1-C_{20})$alkyl, hydroxy$(C_1-C_{20})$alkoxy $(C_1-C_{20})$alkyl, or $(C_3-C_{20})$cycloalkyl; and A is hydrogen, $(C_1-C_{20})$alkyl, $(C_1-C_{20})$ aryl, $(C_1-C_{20})$ alkoxy, $(C_6-C_{20})$aryl$(C_1-C_{20})$alkyl, hydroxy$(C_1-C_{20})$alkyl, hydroxy$(C_1-C_{20})$alkoxy$(C_1-C_{20})$alkyl, $(C_3-C_{20})$cycloalkyl, amino, nitro, cyano, or hydroxy.

As disclosed herein, the terms ⌈alkyl⌋, ⌈alkoxy⌋, and other substituents including an ⌈alkyl⌋ part include both of the straight chain type and the branched chain type, and the term ⌈cycloalkyl⌋ includes polycyclic hydrocarbon as well as monocyclic hydrocarbon. The term ⌈aryl⌋ described herein, which is an organic radical derived from aromatic hydrocarbon by the removal of one hydrogen atom, may include a single ring or a fused ring containing, properly 4 to 7 ring atoms, and preferably 5 or 6 ring atoms in each ring, and include rings in which a plurality of aryl groups are bonded through single bond(s). The term ⌈hydroxyalkyl⌋ means OH-alkyl in which a hydroxy group is bonded to the alkyl group defined above, and the term ⌈hydroxyalkoxyalkyl⌋ means hydroxyalkyl-o-alkyl in which an alkoxy group is bonded to the hydroxyalkyl group.

In addition, '$(C_1-C_{20})$alkyl' may be preferably $(C_1-C_{10})$alkyl, more preferably $(C_1-C_6)$alkyl. '$(C_6-C_{20})$aryl' may be preferably $(C_6-C_{18})$aryl. '$(C_1-C_{20})$alkoxy' may be preferably $(C_1-C_{10})$alkoxy, more preferably $(C_1-C_4)$alkoxy. '$(C_6-C_{20})$aryl$(C_1-C_{20})$alkyl' may be preferably $(C_6-C_{18})$aryl$(C_1-C_{10})$alkyl, more preferably $(C_6-C_{18})$aryl$(C_1-C_6)$alkyl. 'Hydroxy$(C_1-C_{20})$alkyl' may be preferably hydroxy$(C_1-C_{10})$alkyl, more preferably hydroxy$(C_1-C_6)$alkyl. 'Hydroxy$(C_1-C_{20})$alkoxy$(C_1-C_{20})$alkyl' may be preferably hydroxy$(C_1-C_{10})$alkoxy$(C_1-C_{10})$alkyl, more preferably hydroxy$(C_1-C_4)$alkoxy$(C_1-C_6)$alkyl. '$(C_3-C_{20})$cycloalkyl' may be preferably $(C_3-C_{10})$cycloalkyl.

In detail, $R_1$ to $R_3$ each may be independently hydrogen, bromo, chloro, iodo, methyl, ethyl, n-propyl, i-propyl, n-butyl, i-butyl, t-butyl, n-pentyl, i-pentyl, n-hexyl, hexyl, phenyl, naphthyl, biphenyl, terphenyl, anthryl, indenyl, phenanthryl, methoxy, ethoxy, n-propyloxy, propyloxy, n-butoxy, i-butoxy, t-butoxy, hydroxymethyl, hydroxyethyl, hydroxy-n-propyl, hydroxy-n-butyl, hydroxy-i-butyl, hydroxy-n-pentyl, hydroxy-i-pentyl, hydroxy-n-hexyl, hydroxy-i-hexyl, hydroxymethoxymethyl, hydroxymethoxyethyl, hydroxymethoxypropyl, hydroxymethoxybutyl, hydroxyethoxymethyl, hydroxyethoxyethyl, hydroxyethoxypropyl, hydroxyethoxybutyl, hydroxyethoxypentyl, or hydroxyethoxyhexyl; and A may be hydrogen, methyl, ethyl, n-propyl, i-propyl, n-butyl, i-butyl, t-butyl, phenyl, naphthyl, biphenyl, terphenyl, anthryl, indenyl, phenanthryl, methoxy, ethoxy, propyloxy, butoxy, hydroxymethyl, hydroxyethyl, hydroxypropyl, hydroxybutyl, hydroxymethoxymethyl, hydroxymethoxyethyl, hydroxymethoxypropyl, hydroxymethoxybutyl, hydroxyethoxymethyl, hydroxyethoxyethyl, hydroxyethoxypropyl, hydroxyethoxybutyl, amino, nitro, cyano, or hydroxy, but is not limited thereto.

In more detail, $R_1$ may be hydrogen or n-butyl; $R_2$ may be methyl; and $R_3$ may be methyl, n-butyl, or phenyl.

Representative examples of fluorene oxime ester compounds according to the present invention may include the following compounds, but the present invention is not limited to the following compounds.

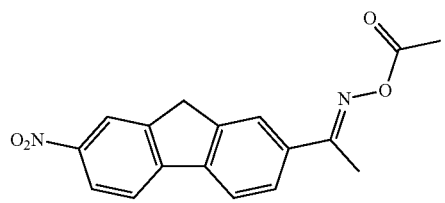

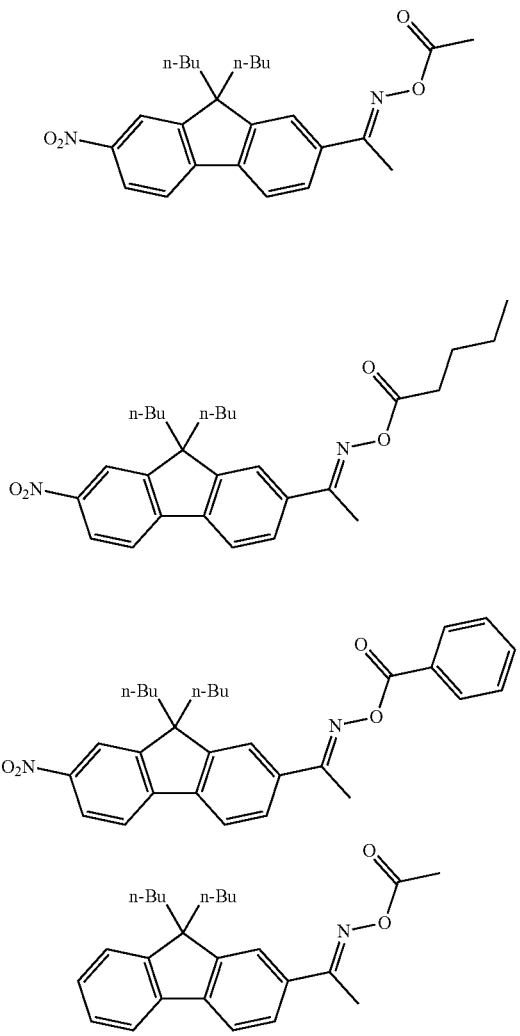

The fluorene oxime ester compound represented by Chemical Formula 1 according to the present invention may be prepared, as shown in the following Scheme 1.

[Scheme 1]

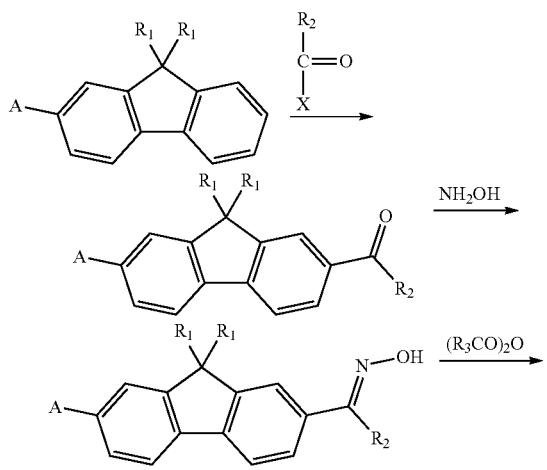

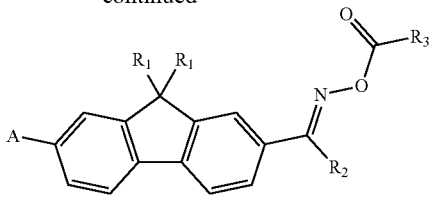

In Scheme 1, $R_1$ to $R_3$ and A have the same definitions as defined in Chemical Formula 1, respectively, and X is halogen.

According to the present invention, the fluorene oxime ester compound represented by Chemical Formula 1 may be contained in the photoresist composition as the photopolymerization initiator.

The photoresist composition according to the present invention may contain the fluorene oxime ester compound represented by Chemical Formula 1, an acrylic polymer or an acrylic polymer having an acrylic unsaturated bond in a side chain, a polymerizable compound having an ethylenically unsaturated bond, a solvent, and the like, and then have excellent control pattern characteristics, and thin film properties such as heat resistance, chemical resistance, and the like.

The acrylic polymer is a copolymer including the following monomers, and examples of the monomer include methyl(meth)acrylate, ethyl(meth)acrylate, propyl(meth)acrylate, butyl(meth)acrylate, pentyl(meth)acrylate, hexyl(meth)acrylate, cyclohexyl(meth)acrylate, heptyl(meth)acrylate, octyl(meth)acrylate, nonyl(meth)acrylate, decyl(meth)acrylate, lauryl(meth)acrylate, dodecyl(meth)acrylate, tetradecyl(meth)acrylate, hexadecyl(meth)acrylate, isobornyl(meth)acrylate, adamantyl(meth)acrylate, dicyclopentanyl(meth)acrylate, dicyclopentenyl(meth)acrylate, benzyl(meth)acrylate, 2-methoxyethyl(meth)acrylate, 2-ethoxyethyl(meth)acrylate, acrylic acid, methacrylic acid, itaconic acid, maleic acid, maleic anhydride, maleic acid monoalkyl ester, monoalkyl itaconate, monoalkyl fumarate, glycidyl acrylate, glycidyl methacrylate, 3,4-epoxybutyl(meth)acrylate, 2,3-epoxycyclohexyl(meth)acrylate, 3,4-epoxycyclohexylmethyl(meth)acrylate, 3-methyloxetane-3-methyl(meth)acrylate, 3-ethyloxetane-3-methyl(meth)acrylate, styrene, α-methylstryene, acetoxystyrene, N-methylmaleimide, N-ethylmaleimide, N-propylmaleimide, N-butylmaleimide, N-cyclohexylmaleimide, (meth)acrylamide, N-methyl(meth)acrylamide, or the like. Among them, one monomer may be used alone, or at least two kinds thereof may be used together.

The acrylic polymer having the acrylic unsaturated bond in the side chain may be a copolymer obtained by an addition reaction of an epoxy resin to an acrylic copolymer containing carboxylic acid. As an example, a binder resin obtained by the addition reaction of the epoxy resin such as glycidyl acrylate, glycidyl methacrylate, 3,4-epoxybutyl(meth)acrylate, 2,3-epoxycyclohexyl(meth)acrylate, 3,4-epoxycyclohexylmethyl(meth)acrylate, or the like, to the acrylic copolymer containing the carboxylic acid obtained by copolymerizing an acrylic monomer containing carboxylic acid such as acrylic acid, methacrylic acid, itaconic acid, maleic acid, maleic acid monoalkyl ester, or the like, and at least two monomers selected from alkyl(meth)acrylate such as methyl(meth)acrylate, hexyl(meth)acrylate, or the like, cyclohexyl(meth)acrylate, isobornyl(meth)acrylate, adamantyl(meth)acrylate, dicyclopentanyl(meth)acrylate, dicyclopentenyl(meth)acrylate, benzyl(meth)acrylate, 2-methoxyethyl(meth)acrylate, 2-ethoxyethyl(meth)acrylate, styrene, α-methylstyrene, acetoxystyrene, N-methylmaleimide, N-ethylmaleimide, N-propylmaleimide, N-butylmaleimide, N-cyclohexylmaleimide, (meth)acrylamide, N-methyl(meth)acrylamide, or the like, at 40 to 180° C. may be used.

As another example, the acrylic polymer having the acrylic unsaturated bond in the side chain may be a copolymer obtained by an addition reaction of carboxylic acid to an acrylic copolymer containing an epoxy group, and a binder resin obtained by the addition reaction of an acryl monomer containing carboxylic acid such as acrylic acid, methacrylic acid, itaconic acid, maleic acid, maleic acid monoalkyl ester, or the like, to the acrylic copolymer containing epoxy group obtained by copolymerizing an acryl monomer containing the epoxy group such as glycidyl acrylate, glycidylmethacrylate, 3,4-epoxybutyl(meth)acrylate, 2,3-epoxycyclohexyl(meth)acrylate, 3,4-epoxycyclohexylmethyl(meth)acrylate, or the like, to at least two or more monomers selected from alkyl(meth)acrylate such as methyl(meth)acrylate, hexyl(meth)acrylate, or the like, cyclohexyl(meth)acrylate, isobornyl(meth)acrylate, adamantyl(meth)acrylate, dicyclopentanyl(meth)acrylate, dicyclopentenyl(meth)acrylate, benzyl(meth)acrylate, 2-methoxyethyl(meth)acrylate, 2-ethoxyethyl(meth)acrylate, styrene, α-methylstyrene, acetoxystyrene, N-methylmaleimide, N-ethylmaleimide, N-propylmaleimide, N-butylmaleimide, N-cyclohexylmaleimide, (meth)acrylamide, N-methyl(meth)acrylamide, or the like, at 40 to 180° C. may be used.

The acrylic polymer or the acrylic polymer having the acrylic unsaturated bond in the side chain used as the binder resin of the photoresist composition may be preferably used at a content of 3 to 50 weight % based on 100 weight % of the photoresist composition in order to control the pattern characteristics and impart the thin film properties such as heat resistance, chemical resistance, and the like. In addition, an average molecular weight thereof may be preferably 2,000 to 300,000, more preferably 4,000 to 100,000, and a dispersion degree thereof may be preferably 1.0 to 10.0.

In the photoresist composition according to the present invention, the polymerizable compound having the ethylenically unsaturated bond may be crosslinked by a photoreaction at the time of forming a pattern to thereby serve to form the pattern and be cross-linked at the time of heating at a high temperature to thereby impart chemical resistance and heat resistance. The polymerizable compound having the ethylenically unsaturated bond may be contained at a content of 0.001 to 40 moles based on 100 moles of the photoresist composition. In the case in which the polymerizable compound having the ethylenically unsaturated bond is excessively added, a crosslinking degree may be excessively high, such that elasticity of the pattern may be decreased. Specific examples of the polymerizable compound having the ethylenically unsaturated bond may include alkyl ester of (meth)acrylic acid such as methyl(meth)acrylate, ethyl(meth)acrylate, butyl(meth)acrylate, 2-ethylhexyl(meth)acrylate, lauryl(meth)acrylate, or the like, glycidyl(meth)acrylate, polyethylene glycolmono(meth)acrylate having 2 to 14 ethyleneoxide groups, ethyleneglycoldi(meth)acrylate, polyethyleneglycoldi(meth)acrylate having 2 to 14 ethylene oxide groups, propyleneglycoldi(meth)acrylate having 2 to 14 propyleneoxide groups, trimethylolpropanedi(meth)acrylate, bisphenol A diglycidyletheracrylic acid adduct, phthalic acid diester of β-hydroxyethyl(meth)acrylate, toluenediisocyanate adduct of β-hydroxyethyl(meth)acrylate, a compound obtained by esterifying polyhydric alcohol with α,β-unsaturated carboxylic acid such as trimethylolpropanetri(meth)acrylate, pentaerythritoltri(meth)acrylate, pentaerythritoltetra(meth)acrylate, dipentaerythritolpenta(meth)acrylate, dipentaerythritolhexa(meth)acrylate, dipentaerythritoltri(meth)acrylate, acrylic acid adducts of polyhydric glycidyl compounds such as trimethylol propane triglycidyl ether acrylic acid adducts, and the like. The polymerizable compounds may be used alone or as mixtures of two or more thereof.

In addition, a content of the fluorene oxime ester compound used as the photoinitiator in the photoresist composition according to the present invention is a content for increasing transparency and minimizing an exposure dose, and it is effective that 0.01 to 10 weight %, preferably 0.1 to 5 weight % of the fluorene oxime ester compound is used based on 100 weight % of the photoresist composition.

Further, the photoresist composition according to the present invention may further contain a silicon based compound having an epoxy or amine group as an adhesion assisting agent, as needed.

The silicon based compound may be further contained in the photoresist composition so as to improve adhesion force between an indium tin oxide (ITO) electrode and the photoresist composition and increase heat resistance after curing. As the silicon based compound having the epoxy or amine group, there are (3-glycidoxypropyl)trimethoxysilane, (3-glycidoxypropyl)triethoxysilane, (3-glycidoxypropyl)methyldimethoxysilane, (3-glycidoxypropyl)methyldiethoxysilane, (3-glycidoxypropyl) dimethylmethoxysilane, (3-glycidoxypropyl)dimethylethoxysilane, 3,4-epoxybutyltrimethoxysilane, 3,4-epoxybutyltriethoxysilane, 2-(3,4-epoxycyclohexyl)ethyltrimethoxysilane, 2-(3,4-epoxycyclohexyl)ethyltriethoxysilane, aminopropyltrimethoxysilane, and the like. The silicon based compounds may be used alone or as mixtures of two or more thereof.

A content of the silicon based compound having the epoxy or amine group may be 0.0001 to 3 weight % based on 100 weight % of the photoresist composition.

In addition, the photoresist composition according to the present invention may further contain additives having compatibility such as a photosensitizer, a thermal polymerization inhibitor, a defoamer, a leveling agent, or the like, as needed.

The method to form a pattern using the photoresist according to the present invention may be conducted as follows. The solution of photoresist composition dissolved in a suitable solvent is applied to the substrate by spin-coating, and it is exposed to ultraviolet light through mask. Then the substrate is developed with an alkaline developer solution. In this case, it is preferable that viscosity is controlled so as to be in a range of 1 to 50 cps by adding 10 to 95 weight % of the solvent based on 100 weight % of the photoresist composition.

Considering compatibility with the binder resin, the photoinitiator, and other compounds, examples of the solvent include ethylacetate, butylacetate, diethylene glycol dimethyl ether, diethylene glycol dimethylethyl ether, methylmethoxy propionate, ethylethoxy propionate (EEP), ethyl lactate, propylene glycol methyl ether acetate (PGMEA), propylene glycol methyl ether propionate (PGMEP), propylene glycol methyl ether, propylene glycol propyl ether, methyl cellosolve acetate, ethyl cellosolve acetate, diethylene glycol methyl acetate, diethylene glycol ethyl acetate, acetone, methyl isobutyl ketone, cyclohexanone, dimethylformamide (DMF), N,N-dimethylacetamide (DMAc), N-methyl-2-pyrrolidone (NMP), γ-butyrolactone, diethyl ether, ethylene glycol dimethyl ether, diglyme, tetrahydrofuran (THF), methanol, ethanol, propanol, iso-propanol, methylcellosolve, ethylcellosolve, diethylene glycol methyl ether, diethylene glycol ethyl ether, dipropylene glycol methyl ether, toluene, xylene, hexane, heptane, octane, or the like. The solvents may be used alone or as mixtures of two or more thereof.

Advantageous Effects

The fluorene oxime ester compound according to the present invention as a photoinitiator of a photoresist composition may have significantly excellent sensitivity even at a small amount and have excellent physical properties such as a residual film thickness, pattern stability, chemical resistance, elasticity, and the like, such that out-gassing generated from the photoinitiator during an exposure process and a post-bake process in the thin film transistor liquid crystal display (TFT-LCD) manufacturing process may be minimized, which may decrease contamination, thereby making it possible to minimize defects that will be generated due to the contamination.

DETAILED DESCRIPTION OF EMBODIMENTS

Hereinafter, a representative compound according to the present invention will be described in detail with reference to the Examples and Comparative Examples. However, Examples of the present invention may be modified in several different forms, and the scope of the present invention is not construed as being limited to Examples described below. Rather, Examples are provided so that this disclosure will be thorough and complete, and will fully convey the concept of the invention to those skilled in the art.

Example 1

Preparation of 1-(9,9-H-7-nitrofluorene-2-yl)-ethanone oxime-O-acetate

Reaction 1. Synthesis of 1-(9,9-H-7-nitrofluorene-2-yl)-ethanone

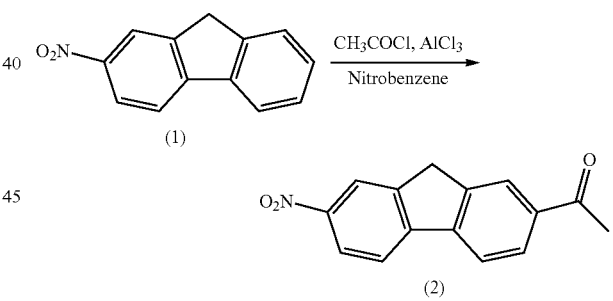

After 5.0 g of 2-nitrofluorene (1) (23.7 mmol) was dissolved in 100 ml of anhydrous nitrobenzene and 6.31 g of anhydrous aluminum chloride (47.4 mmol) was added thereto, the reaction mixture was heated to 45° C., and a solution in which 2.79 g of acetyl chloride (35.5 mmol) was dissolved in 30 ml of anhydrous nitrobenzene was slowly added thereto for 30 minutes, followed by stirring at 65° C. for 1 hour. Then the reaction mixture was cooled to room temperature and 70 ml of distilled water was added thereto and stirred for about 30 minutes, followed by filtering the product. The obtained solid product was dispersed in 50 ml of ether and stirred at room temperature for 30 minutes, followed by filtering and drying, thereby obtaining 5.08 g of 1-(9,9-H-7-nitrofluorene-2-yl)-ethanone (2) (84.7%) as a light yellow product.

$^1$H NMR (δ ppm; DMSO-$d_6$): 2.64 (3H, s), 4.18 (2H, s), 8.06 (1H, dd), 8.21-8.32 (4H, m), 8.51 (1H, d)

MS(m/e):253

Reaction 2. Synthesis of 1-(9,9-H-7-nitrofluorene-2-yl)-ethanone oxime

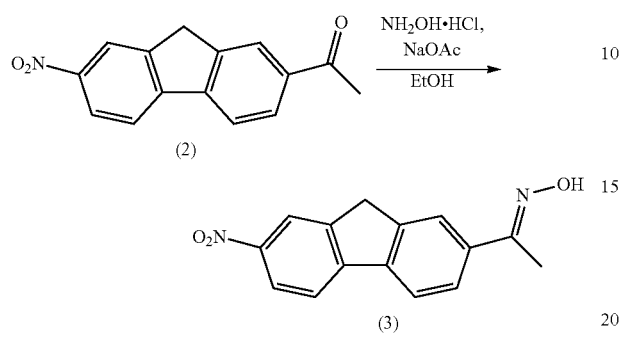

After 1.5 g of 1-(9,9-H-7-nitrofluorene-2-yl)-ethanone (2) (5.92 mmol) was dispersed in 30 ml of ethanol and 0.49 g of hydroxylamine hydrochloride (7.1 mmol) and 0.58 g of sodium acetate (7.1 mmol) were added thereto, the reaction mixture was slowly heated and refluxed for 2 hours. The reaction mixture was cooled to room temperature and 20 ml of distilled water was added thereto, followed by stirring for 30 minutes. The resulting solid was filtered and washed with distilled water several times, followed by drying, thereby obtaining 1.38 g of 1-(9,9-H-7-nitrofluorene-2-yl)-ethanone oxime (3) (86.8%) as a light grey product.

$^1$H NMR ($\delta$ ppm; DMSO-$d_6$): 2.21 (3H, s), 4.09 (2H, s), 7.76 (1H, dd), 7.93 (1H, s), 8.05 (1H, d), 8.12 (1H, d), 8.28 (1H, dd), 8.43 (1H, d), 11.32 (1H, s)

MS(m/e):268

Reaction 3. Synthesis of 1-(9,9-H-7-nitrofluorene-2-yl)-ethanone oxime-O-acetate

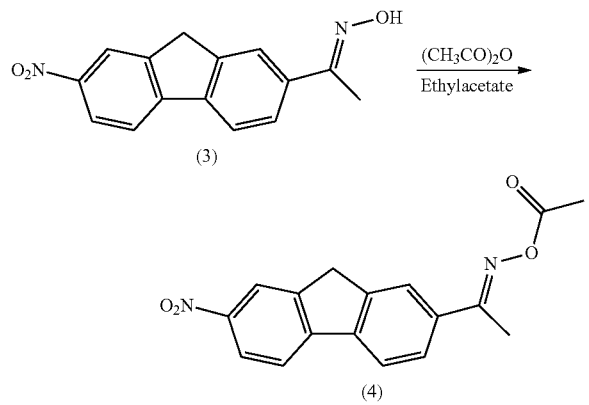

After 1.20 g of 1-(9,9-H-7-nitrofluorene-2-yl)-ethanone oxime (3) (4.47 mmol) was dispersed in 50 ml of ethylacetate and 0.69 g of acetic anhydride (6.76 mmol) was added thereto, the reaction mixture was slowly heated and refluxed for 3 hours. Thereafter, the reaction mixture was cooled to room temperature and sequentially washed with 20 ml of saturated aqueous sodium bicarbonate solution and 20 ml of distilled water. Then, a product obtained by drying the recovered organic layer over anhydrous magnesium sulfate and distilling a solvent under reduced pressure was re-crystallized with 20 ml of methanol, thereby obtaining 1.22 g of 1-(9,9-H-7-nitrofluorene-2-yl)-ethanone oxime-O-acetate (4) (87.9%) as a light yellow product.

$^1$H NMR ($\delta$ ppm; DMSO-$d_6$): 2.24 (3H, s), 2.43 (3H, s), 4.16 (2H, s), 7.88 (1H, d), 8.08 (1H, s), 8.16-8.28 (3H, m), 8.32 (1H, dd), 8.48 (1H, s)

UV($\lambda$max): 337 nm

MS(m/e):310

Example 2

Preparation of 1-(9,9-di-n-butyl-7-nitrofluorene-2-yl)-ethanone oxime-O-acetate

Reaction 1. Synthesis of 9,9-di-n-butyl-2-nitrofluorene

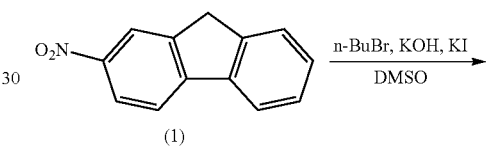

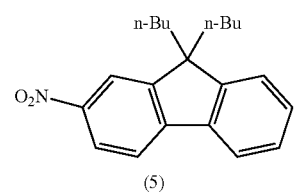

12.66 g of 2-nitrofluorene (1) (60 mmol), 21.0 g of potassium hydroxide (0.3 mol, purity: 80%), and 1.01 g of potassium iodide (6 mmol) were dissolved in 200 ml of anhydrous dimethylsulfoxide under nitrogen atmosphere, and a reaction temperature was maintained at 15° C. Then, 33 ml of n-bromobutane (0.3 mol) was slowly added thereto for 2 hours, followed by stirring at 15° C. for 1 hour. Thereafter, 200 ml of distilled water was added to the reaction mixture and stirred for about 30 minutes, a product was extracted with 300 ml of dichloromethane, and the extracted organic layer was washed with 100 ml of distilled water three times. Then, the recovered organic layer was dried over anhydrous magnesium sulfate, and the solvent was distilled under reduced pressure. The obtained product was purified using a silica gel column chromatography (eluent: dichloromethane:n-hexane=20:1), thereby obtaining 15.4 g of 9,9-di-n-butyl-2-nitrofluorene (5) (79.5%) as a light yellow product.

$^1$H NMR ($\delta$ ppm; CDCl$_3$): 0.52-0.61 (4H, m), 0.66 (6H, t), 1.07 (4H, sex), 2.00-2.06 (4H, m), 7.38-7.42 (3H, m), 7.77-7.80 (2H, d), 8.20 (1H, d), 8.26 (1H, dd)

MS(m/e):323

Reaction 2. Synthesis of 1-(9,9-di-n-butyl-7-nitrof-luorene-2-yl)-ethanone

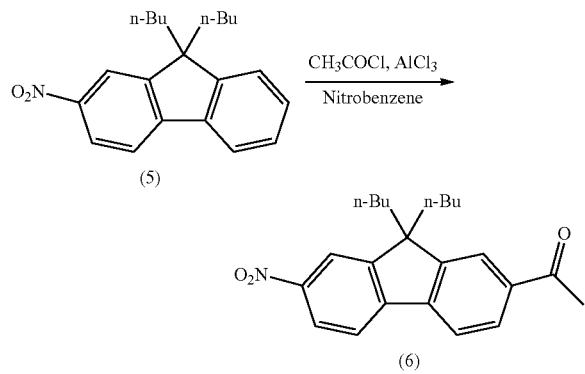

After 7.0 g of 9,9-di-n-butyl-2-nitrofluorene (5) (21.7 mmol) was dissolved in 200 ml of anhydrous nitrobenzene and 5.77 g of anhydrous aluminum chloride (43.4 mmol) was added thereto, the reaction mixture was heated to 45° C., and a solution in which 3.40 g of acetyl chloride (43.3 mmol) was dissolved in 40 ml of anhydrous nitrobenzene was slowly added thereto for 1 hour, followed by stirring at 65° C. for 1 hour. Thereafter, the reaction mixture was cooled to room temperature, 100 ml of distilled water was added thereto and stirred for about 30 minutes, followed by extracting the product with 200 ml of dichloromethane. The extracted organic layer was sequentially washed with 100 ml of saturated aqueous sodium bicarbonate solution and 100 ml of distilled water. Then, a solid product obtained by drying the recovered organic layer over anhydrous magnesium sulfate and distilling a solvent under reduced pressure was dispersed in a small amount of ether and stirred at room temperature for 30 minutes, followed by filtering and drying, thereby obtaining 5.44 g of 1-(9,9-di-n-butyl-7-nitrofluorene-2-yl)-ethanone (6) (68.7%) as a light yellow product.

$^1$H NMR (δ ppm; DMSO-$d_6$): 0.36-0.40 (4H, m), 0.56 (6H, t), 0.96 (4H, sex), 2.04-2.13 (4H, m), 2.62 (3H, s), 8.00-8.05 (2H, m), 8.10-8.18 (2H, m), 8.24-8.27 (1H, m), 8.36 (1H, s)
MS(m/e):365

Reaction 3. Synthesis of 1-(9,9-di-n-butyl-7-nitrof-luorene-2-yl)-ethanone oxime

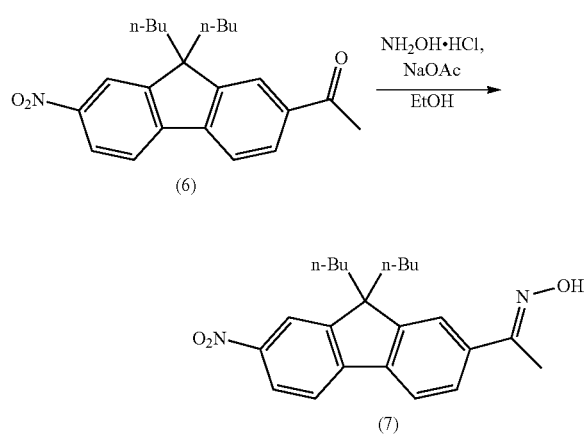

After 5.0 g of 1-(9,9-di-n-butyl-7-nitrofluorene-2-yl)-ethanone (6) (13.7 mmol) was dispersed in 150 ml of ethanol and 1.04 g of hydroxylamine hydrochloride (15.1 mmol) and 1.24 g of sodium acetate (15.1 mmol) were added thereto, the reaction mixture was slowly heated and refluxed for 1 hour. The reaction mixture was cooled to room temperature and 100 ml of distilled water was added thereto. Then, a solid product obtained by stirring the reaction mixture for about 30 minutes was filtered and washed with distilled water several times, followed by drying, thereby obtaining 4.89 g of 1-(9, 9-di-n-butyl-7-nitrofluorene-2-yl)-ethanone oxime (7) (93.9%) as a light yellow product.

$^1$H NMR (δ ppm; DMSO-$d_6$): 0.38-0.48 (4H, m), 0.59 (6H, t), 0.98 (4H, sex), 1.99-2.18 (4H, m), 2.21 (3H, s), 7.69 (1H, dd), 7.80 (1H, s), 7.99 (1H, d), 8.08 (1H, d), 8.25 (1H, dd), 8.33 (1H, d), 11.33 (1H, s)
MS(m/e):380

Reaction 4. Synthesis of 1-(9,9-di-n-butyl-7-nitrof-luorene-2-yl)-ethanone oxime-O-acetate

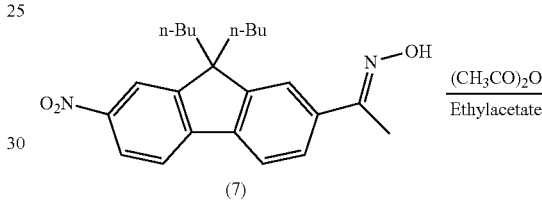

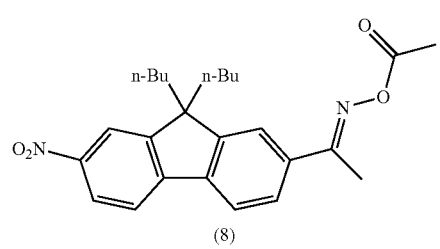

After 1.50 g of 1-(9,9-di-n-butyl-7-nitrofluorene-2-yl)-ethanone oxime (7) (39.5 mmol) was dispersed in 30 ml of ethylacetate and 0.45 g of acetic anhydride (4.4 mmol) was added thereto, the reaction mixture was slowly heated and refluxed for 3 hours. The reaction mixture was cooled to room temperature and sequentially washed with 100 ml of saturated aqueous sodium bicarbonate solution and 100 ml of distilled water. Then, a product obtained by drying the recovered organic layer over anhydrous magnesium sulfate and distilling a solvent under reduced pressure was re-crystallized with 20 ml of methanol, thereby obtaining 1.23 g of 1-(9,9-di-n-butyl-7-nitrofluorene-2-yl)-ethanone oxime-0-acetate (8) (73.8%) as a light yellow product.

$^1$H NMR (δ ppm; CDCl$_3$): 0.48-0.58 (4H, m), 0.67 (6H, t), 1.08 (4H, sex), 2.03-2.09 (4H, m), 2.30 (3H, s), 2.47 (3H, s), 7.77-7.84 (4H, m), 8.22 (1H, d), 8.26 (1H, dd)

UV(λmax): 345 nm
MS(m/e):422

Example 3

Preparation of 1-(9,9-di-n-butyl-7-nitrofluorene-2-yl)-ethanone oxime-O-valerate

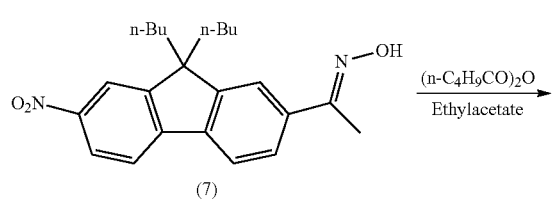

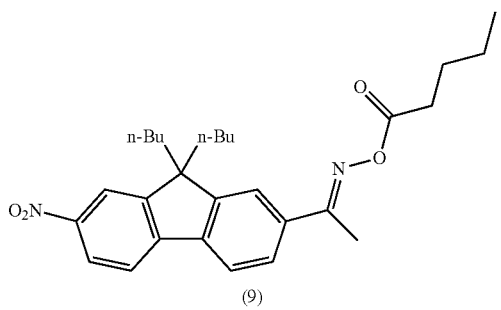

After 1.50 g of 1-(9,9-di-n-butyl-7-nitrofluorene-2-yl)-ethanone oxime (7) (39.5 mmol) was dispersed in 30 ml of ethylacetate and 0.88 g of valeric anhydride (4.7 mmol) was added thereto, the reaction mixture was slowly heated and refluxed for 3 hours. The reaction mixture was cooled to room temperature and sequentially washed with 100 ml of saturated aqueous sodium bicarbonate solution and 100 ml of distilled water. Then, a product obtained by drying the recovered organic layer over anhydrous magnesium sulfate and distilling a solvent under reduced pressure was re-crystallized with 20 ml of methanol, thereby obtaining 0.91 g of 1-(9,9-di-n-butyl-7-nitrofluorene-2-yl)-ethanone oxime-O-valerate (9) (49.7%) as a light yellow product.

$^1$H NMR (δ ppm; CDCl$_3$): 0.49-0.61 (4H, m), 0.68 (6H, t), 0.96 (3H, t), 1.05 (4H, sex), 1.45 (2H, sex), 1.74 (2H, quint), 2.03-2.11 (4H, m), 2.46 (3H, s), 2.55 (2H, t), 7.78-7.86 (4H, m), 8.22 (1H, d), 8.28 (1H, dd)

UV(λmax): 345 nm

MS(m/e):464

Example 4

Preparation of 1-(9,9-di-n-butyl-7-nitrofluorene-2-yl)-ethanone oxime-O-benzoate

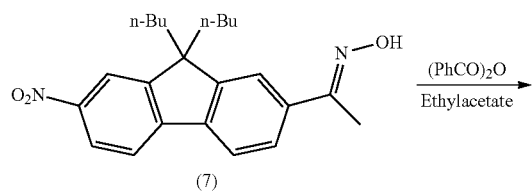

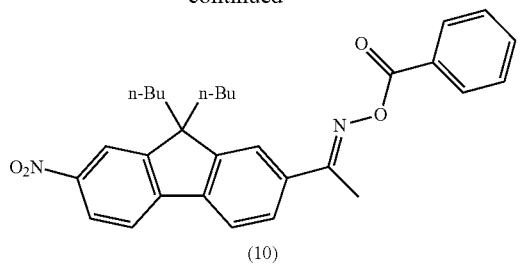

After 1.50 g of 1-(9,9-di-n-butyl-7-nitrofluorene-2-yl)-ethanone oxime (7) (39.5 mmol) was dispersed in 30 ml of ethylacetate and 1.07 g of benzoic anhydrid (4.7 mmol) was added thereto, the reaction mixture was slowly heated and refluxed for 3 hours. The reaction mixture was cooled to room temperature and sequentially washed with 100 ml of saturated aqueous sodium bicarbonate solution and 100 ml of distilled water. Then, a product obtained by drying the recovered organic layers over anhydrous magnesium sulfate and distilling a solvent under reduced pressure was re-crystallized with 20 ml of methanol, thereby obtaining 1.71 g of 1-(9,9-di-n-butyl-7-nitrofluorene-2-yl)-ethanone oxime-O-benzoate (10) (89.4%) as a light green product.

$^1$H NMR (δ ppm; DMSO-d$_6$): 0.39-0.51 (4H, m), 0.60 (6H, t), 1.02 (4H, sex), 2.10-2.21 (4H, m), 2.60 (3H, s), 7.48 (1H, t), 7.61 (2H, t), 7.89-7.98 (3H, m), 8.09-8.18 (3H, m), 8.28 (1H, dd), 8.38 (1H, d)

UV(λmax): 346 nm

MS(m/e):484

Example 5

Preparation of 1-(9,9-di-n-butylfluorene-2-yl)-ethanone oxime-O-acetate

Reaction 1. Synthesis of 1-(9,9-di-n-butylfluorene-2-yl)-ethanone

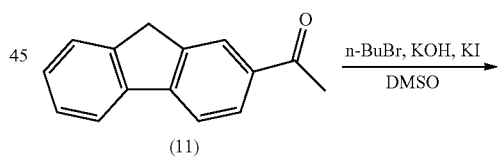

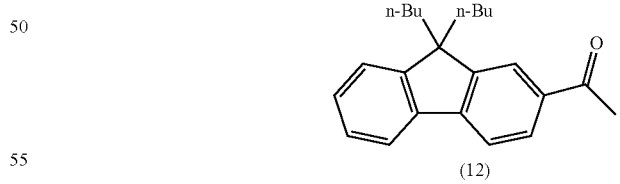

15.9 g of 2-acetylfluorene (11) (76.4 mmol), 18.9 g of potassium hydroxide (0.27 mol, purity: 80%), and 1.26 g of potassium iodide (7.6 mmol) were dissolved in 350 ml of anhydrous dimethylsulfoxide under nitrogen atmosphere, and a reaction temperature was maintained at 15° C. Then, 33 ml of n-bromobutane (0.3 mol) was slowly added thereto for 2 hours, followed by stirring at 15° C. for 1 hour. Thereafter 200 ml of distilled water was added to the reaction mixture and stirred for about 30 minutes, a product was extracted with 300 ml of dichloromethane, and the extracted organic layer was washed with 100 ml of distilled water three times. Then, the recovered organic layer was dried over anhydrous magnesium sulfate, and the solvent was distilled under reduced pressure. The obtained product was purified using a silica gel column chromatography (developing solvent: dichloromethane:n-hexane=15:1), thereby obtaining 22.2 g of 1-(9,9-di-n-butylfluorene-2-yl)-ethanone (12) (90.8%) as a light yellow liquid.

$^1$H NMR (δ ppm; CDCl$_3$): 0.50-0.59 (4H, m), 0.64 (6H, t), 1.06 (4H, sex), 1.98-2.06 (4H, m), 2.66 (3H, s), 7.33-7.38 (3H, m), 7.73-7.77 (2H, m), 7.94-7.97 (2H, m)

MS(m/e):320

Reaction 2. Synthesis of 1-(9,9-di-n-butylfluorene-2-yl)-ethanone oxime

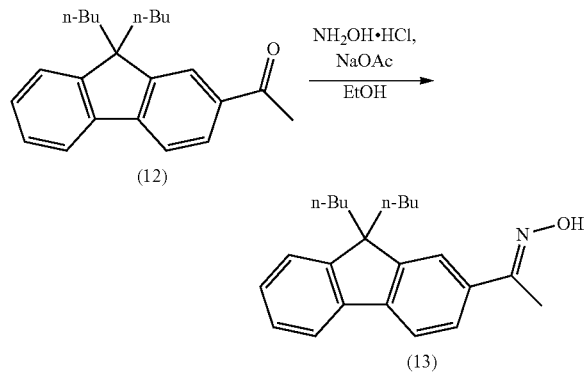

After 5.45 g of 1-(9,9-di-n-butylfluorene-2-yl)-ethanone (12) (17 mmol) was dispersed in 50 ml of ethanol and 1.42 g of hydroxylamine hydrochloride (20.4 mmol) and 1.67 g of sodium acetate (20.4 mmol) were added thereto, the reaction mixture was slowly heated and refluxed for 1 hour. The reaction mixture was cooled to room temperature, and 100 ml of distilled water was added thereto and stirred for about 30 minutes. Then, the product was extracted with 200 ml of ethylacetate and sequentially washed with saturated aqueous sodium bicarbonate solution and 100 ml of distilled water, and the recovered organic layer was dried over anhydrous magnesium sulfate, followed by distilling the solvent under reduced pressure. The obtained solid product was dried, thereby obtaining 4.97 g of 1-(9,9-di-n-butylfluorene-2-yl)-ethanone oxime (13) (87.3%) as a light yellow product.

$^1$H NMR (δ ppm; CDCl$_3$): 0.56-0.64 (4H, m), 0.68 (6H, t), 1.06 (4H, sex), 1.96-2.05 (4H, m), 2.37 (3H, s), 7.32-7.38 (3H, m), 7.59-7.64 (2H, m), 7.69-7.75 (2H, m), 8.45 (1H, br.s)

MS(m/e):335

Reaction 3. Synthesis of 1-(9,9-di-n-butylfluorene-2-yl)-ethanone oxime-O-acetate

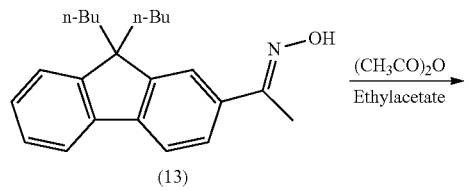

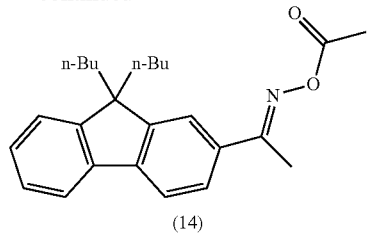

After 2.01 g of 1-(9,9-di-n-butylfluorene-2-yl)-ethanone oxime (13) (6.0 mmol) was dispersed in 50 ml of ethylacetate and 0.91 g of acetic anhydrid (8.9 mmol) was added thereto, the reaction mixture was slowly heated and refluxed for 1 hour. The reaction mixture was cooled to room temperature and sequentially washed with 100 ml of saturated aqueous sodium bicarbonate solution and 100 ml of distilled water. Then, a solid product obtained by drying the recovered organic layer over anhydrous magnesium sulfate and distilling a solvent under reduced pressure was re-crystallized with 25 ml of methanol, thereby obtaining 2.03 g of 1-(9,9-di-n-butylfluorene-2-yl)-ethanone oxime-O-acetate (14) (89.7%) as a light yellow product.

$^1$H NMR (δ ppm; CDCl$_3$): 0.53-0.59 (4H, m), 0.65 (6H, t), 1.06 (4H, sex), 1.96-2.04 (4H, m), 2.29 (3H, s), 2.45 (3H, s), 7.34-7.35 (3H, m), 7.70-7.74 (4H, m)

UV(λmax): 323 nm

MS(m/e):377

Example 6

Preparation of Binder Resin a) Preparation of Binder Resin 1

After 200 ml of propylene glycol methyl ether acetate and 1.5 g of azobisisobutyronitrile (AIBN) were added to a 500 ml polymerization reactor, methacrylic acid, glycidylmethacrylate, methylmethacrylate, and dicyclopentanylacrylate were added thereto at a molar ratio of 20:20:40:20 so that a solid content of the monomer was weight %. Thereafter, the reaction mixture was polymerized while stirring them at 70° C. for 5 hours under nitrogen atmosphere, thereby preparing a binder resin 1, which is an acrylic polymer. It was confirmed that the copolymer prepared as described above had an average molecular weight of 25,000 and a dispersion degree of 2.0.

b) Preparation of Binder Resin 2

After 200 ml of propylene glycol methyl ether acetate and 1.0 g of AIBN were added to a 500 ml polymerization reactor, methacrylic acid, styrene, methylmethacrylate, and cyclohexylmethacrylate were added thereto at a molar ratio of 40:20:20:20 so that a solid content of the monomer was weight %. Thereafter, the reaction mixture was polymerized, followed by stirring at 70° C. for 5 hours under nitrogen atmosphere, thereby synthesizing a copolymer. 0.3 g of N,N-dimethylaniline and 20 moles of glycidylmethacrylate were added to this reactor, based on 100 moles of the solid content of the total monomer and stirred at 100° C. for 10 hours, thereby preparing a binder resin 2, which was an acrylic polymer having an acrylic unsaturated bond in a side chain. It was confirmed that the copolymer prepared as described above had an average molecular weight of 20,000 and a dispersion degree of 2.1.

Examples 7 to 16

Preparation of Photoresist Composition

The binder resin 1 to 2; a photoreactive compound; Compound 8, 9, 10, or 14 as a photoinitiator; and FC-430 (a leveling agent from 3M 0.1 weight %) were sequentially added to a reactor equipped with a UV-protecting layer and a stirrer according to the constituents and contents shown in the following Table 1 and stirred at room temperature. Thereafter, propylene glycol methyl ether acetate (PGMEA) was added thereto as a solvent so that the entire content was 100 weight %, thereby preparing the photoresist composition.

Examples 17

Preparation of Photoresist Composition for Black Matrix 20 weight % of the binder resin 1, 10 weight % of dipentaerythritol hexaacrylate, 0.5 weight % of Compound 9, 50 weight % of carbon black dispersed in PGMEA at a solid content of 25 weight %, and 0.1 weight % of FC-430 (leveling agent from 3M) were sequentially added to a reactor equipped with a UV-protecting layer and a stirrer and stirred at room temperature. Thereafter, PGMEA was added thereto as the solvent so that the entire content was 100 weight %, thereby preparing the photoresist composition for a black matrix.

Examples 18

Preparation of Red Photoresist Composition

The Red photoresist composition was prepared by the same method as that in Example 17 except that 50 weight % of Pigment Red 177 (P.R. 177) dispersion solution having a solid content of 25 weight % was used instead of the carbon black.

TABLE 1

| Example | Binder resin (weight %) | Photoreactive compound (weight %) | Photoinitiator (weight %) | Additive (weight %) |
|---|---|---|---|---|
| 7 | 1 (40) | Dipentaerythritol hexaacrylate (20) | Compound 8 (0.5) | FC-430 (0.1) |
| 8 | 1 (40) | Pentaerythritol triacrylate (20) | Compound 9 (0.5) | FC-430 (0.1) |
| 9 | 1 (40) | Trimethylolpropane triacrylate (10) Ethyleneglycol-diacrylate (10) | Compound 10 (0.5) | FC-430 (0.1) |
| 10 | 1 (40) | Dipentaerythritol pentaacrylate (20) | Compound 14 (0.5) | FC-430 (0.1) |
| 11 | 1 (40) | Bisphenol A diglycidylether acrylic acid adduct (20) | Compound 8 (0.5) | FC-430 (0.1) |
| 12 | 2 (40) | Trimethylolpropane triacrylate (20) | Compound 9 (0.5) | FC-430 (0.1) |
| 13 | 2 (40) | Pentaerythritol triacrylate (20) | Compound 10 (0.5) | FC-430 (0.1) |
| 14 | 2 (40) | Ethyleneglycol dimethacrylate (20) | Compound 14 (0.5) | FC-430 (0.1) |
| 15 | 1 (20) 2 (20) | Dipentaerythritol tetraacrylate (20) | Compound 8 (0.5) | FC-430 (0.1) |
| 16 | 1 (20) 2 (20) | Pentaerythritol tetraacrylate (20) | Compound 9 (0.5) | FC-430 (0.1) |
| 17 | 1 (20) | Dipentaerythritol hexaacrylate (10) | Compound 9 (0.5) | FC-430 (0.1) Carbon black (50) |
| 18 | 1 (20) | Dipentaerythritol hexaacrylate (10) | Compound 9 (0.5) | FC-430 (0.1) P.R.177 (50) |

Comparative Example 1

Preparation of Photoresist Composition

The photoresist composition was prepared by the same method as in Example 7 except for using 1,2-Octanedione-1-[4-(phenylthio)phenyl]-2-(O-benzoyloxime) as a photoinitiator instead of Compound 8.

Comparative Example 2

Preparation of Photoresist Composition

The photoresist composition was prepared by the same method as in Example 7 except for using the following Compound 21 as a photoinitiator instead of Compound 8.

[Compound 21]

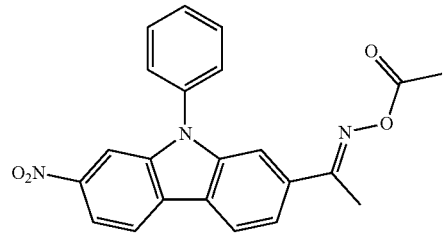

Comparative Example 3

Preparation of Photoresist Composition

The photoresist composition was prepared by the same method as in Example 7 except for using the following Compound 22 as a photoinitiator instead of Compound 8.

[Compound 22]

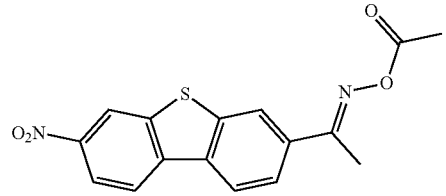

Comparative Example 4

Preparation of Photoresist Composition

The photoresist composition was prepared by the same method as in Example 7 except for using the following Compound 23 as a photoinitiator instead of Compound 8.

[Compound 23]

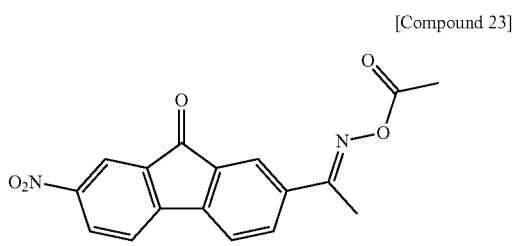 [SMILES: CC(=O)O/N=C(\C)c1ccc2c(c1)C(=O)c1cc([N+](=O)[O-])ccc1-2]

Experimental Example

Evaluation of Photoresist Composition

Evaluation of the photoresist compositions prepared in Examples 7 to 18 and Comparative Examples 1 to 4 was performed on a glass substrate. Performances of the photoresist composition such as sensitivity, a residual film thickness, pattern stability, chemical resistance, elasticity, and the like, were measured, and the result was shown in the following Table 2.

1) Sensitivity

After the photoresist was spin-coated onto the glass substrate and dried at 100° C. for 1 minute on a hotplate, the dried photoresist was exposed using a step mask and then developed in 0.04% KOH aqueous solution. An exposure dose at which a thickness of a step mask pattern was maintained at 80% of an initial thickness was evaluated as the sensitivity.

2) Residual Film Thickness

After the photoresist composition was coated onto a substrate using a spin coater and prebaked at 100° C. for 1 minute, the prebaked photoresist was exposed at 365 nm and then postbaked at 230° C. for 20 minutes. Then, a thickness ratio (%) of a photoresist film before and after post-baking was measured.

3) Pattern Stability

A silicon wafer formed with the photoresist pattern was cut in a perpendicular direction of a hole pattern and observed in a cross-sectional direction of the pattern using an electron microscope. When a side wall of the pattern was erected at an angle of 55° or more against the substrate and reduction of the film thickness was not observed, the pattern stability of the photoresist composition was judged as 'good', and when the reduction of the film thickness was observed, the pattern stability was judged as 'reduction of film thickness'.

4) Chemical Resistance

The photoresist composition was coated onto a substrate using a spin coater, and then a photoresist film was formed through processes such as a prebake process, a postbake process, and the like. After the formed photoresist film was dipped into a stripper solution at 40° C. for 10 minutes, whether transmittance and a thickness of the photoresist film were changed or not was observed. When the change in the transmittance and the thickness was 2% or less, the chemical resistance was judged as 'good', and when the change in the transmittance and the thickness was 2% or more, the chemical resistance was judged as 'bad'.

5) Elasticity

After the photoresist composition was coated onto a substrate using a spin coater and pre-baked at 1000 for 1 minute, the prebaked photoresist was exposed at the sensitivity of the photoresist and then developed in a KOH aqueous solution to form a pattern (20 μm×20 μm). The formed pattern was postbaked at 230° C. for 20 minutes to thereby be crosslinked to each other, and elasticity of the pattern was measured using a nano indentor. As a result measured by the nano indentor, when the total changed amount by 5 g·f loading was 500 nm or more, the elasticity was judged as 'good', and when the total changed amount is 500 nm or less, the elasticity was judged as 'bad'.

TABLE 2

| Classification | Sensitivity (mJ/cm$^2$) | residual film thickness (%) | Pattern stability | Chemical resistance | elasticity |
|---|---|---|---|---|---|
| Example 7 | 40 | 91 | Good | Good | Good |
| Example 8 | 50 | 92 | Good | Good | Good |
| Example 9 | 45 | 91 | Good | Good | Good |
| Example 10 | 55 | 90 | Good | Good | Good |
| Example 11 | 35 | 93 | Good | Good | Good |
| Example 12 | 40 | 91 | Good | Good | Good |
| Example 13 | 40 | 91 | Good | Good | Good |
| Example 14 | 50 | 92 | Good | Good | Good |
| Example 15 | 30 | 93 | Good | Good | Good |
| Example 16 | 35 | 93 | Good | Good | Good |
| Example 17 | 60 | 90 | Good | Good | Good |
| Example 18 | 60 | 91 | Good | Good | Good |
| Comparative Example 1 | 200 | 87 | Reduction of film thickness | bad | Good |
| Comparative Example 2 | 80 | 88 | Good | bad | bad |
| Comparative Example 3 | 120 | 84 | Reduction of film thickness | bad | Good |
| Comparative Example 4 | 100 | 85 | Reduction of film thickness | bad | Good |

As shown in Table 2, it may be appreciated that the fluorene oxime ester compounds according to the present invention and the photoresist composition using the fluorene oxime ester compounds as the photopolymerization initiator had significantly excellent sensitivity and excellent physical properties such as the residual film thickness, the pattern stability, the chemical resistance, the elasticity, and the like, as compared with the compound not containing the fluorene group and the photoresist composition using the compound (Comparative Examples 1 to 4) as the photopolymerization initiator. Therefore, out-gassing generated from the photoinitiator during the exposure process and the postbake process in the thin film transistor liquid crystal display (TFT-LCD) manufacturing process may be minimized, such that contamination may be decreased, thereby making it possible to minimize defects that will be generated due to the contamination.

The invention claimed is:
1. A fluorene oxime ester compound represented by the following Chemical Formula 1:

[Chemical Formula 1]

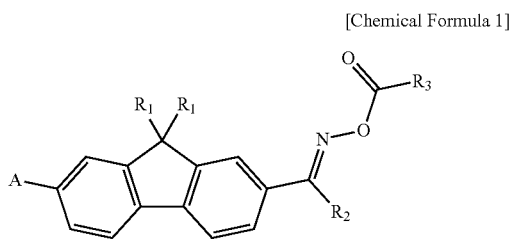

where,
each $R_1$ is independently $(C_1-C_{20})$alkyl;
$R_2$ is hydrogen, halogen, $(C_1-C_{20})$alkyl, $(C_6-C_{20})$aryl, $(C_1-C_{20})$alkoxy, $(C_6-C_{20})$aryl$(C_1-C_{20})$alkyl, hydroxy$(C_1-C_{20})$alkyl, hydroxy$(C_1-C_{20})$alkoxy$(C_1-C_{20})$alkyl, or $(C_3-C_{20})$cycloalkyl;
$R_3$ is $(C_1-C_{20})$alkyl, $(C_6-C_{20})$aryl, $(C_1-C_{20})$alkoxy, $(C_6-C_{20})$aryl$(C_1-C_{20})$alkyl, hydroxy$(C_1-C_{20})$alkyl, hydroxy$(C_1-C_{20})$alkoxy$(C_1-C_{20})$alkyl, or $(C_3-C_{20})$cycloalkyl; and
A is hydrogen, $(C_1-C_{20})$alkyl, $(C_6-C_{20})$aryl, $(C_1-C_{20})$alkoxy, $(C_6-C_{20})$aryl$(C_1-C_{20})$alkyl, hydroxy$(C_1-C_{20})$alkyl, hydroxy$(C_1-C_{20})$alkoxy$(C_1-C_{20})$alkyl, $(C_3-C_{10})$cycloalkyl, amino, nitro, cyano, or hydroxyl.

2. The fluorene oxime ester compound of claim 1, wherein each $R_1$ is independently methyl, ethyl, n-propyl, i-propyl, n-butyl, i-butyl, t-butyl, n-pentyl, i-pentyl, n-hexyl, or i-hexyl;
$R_2$ is hydrogen, bromo, chloro, iodo, methyl, ethyl, n-propyl, i-propyl, n-butyl, i-butyl, t-butyl, n-pentyl, i-pentyl, n-hexyl, i-hexyl, phenyl, naphthyl, biphenyl, terphenyl, anthryl, indenyl, phenanthryl, methoxy, ethoxy, n-propyloxy, i-propyloxy, n-butoxy, i-butoxy, t-butoxy, hydroxymethy, hydroxyethyl, hydroxy-n-propyl, hydroxy-n-butyl, hydroxy-i-butyl, hydroxy-n-pentyl, hydroxy-i-pentyl, hydroxy-n-hexyl, hydroxy-i-hexyl, hydroxymethoxymethyl, hydroxymethoxyethyl, hydroxymethoxypropyl, hydroxymethoxybutyl, hydroxyethoxymethyl, hydroxyethoxyethyl, hydroxyethoxypropyl, hydroxyethoxybutyl, hydroxyethoxypentyl, or hydroxyethoxyhexyl;
$R_3$ is bromo, chloro, iodo, methyl, ethyl, n-propyl, i-propyl, n-butyl, i-butyl, t-butyl, n-pentyl, i-pentyl, n-hexyl, i-hexyl, phenyl, naphthyl, biphenyl, terphenyl, anthryl, indenyl, phenanthryl, methoxy, ethoxy, n-propyloxy, i-propyloxy, n-butoxy, i-butoxy, t-butoxy, hydroxymethy, hydroxyethyl, hydroxy-n-propyl, hydroxy-n-butyl, hydroxy-i-butyl, hydroxy-n-pentyl, hydroxy-i-pentyl, hydroxy-n-hexyl, hydroxy-i-hexyl, hydroxymethoxymethyl, hydroxymethoxyethyl, hydroxymethoxypropyl, hydroxymethoxybutyl, hydroxyethoxymethyl, hydroxyethoxyethyl, hydroxyethoxypropyl, hydroxyethoxybutyl, hydroxyethoxypentyl, or hydroxyethoxyhexyl; and
A is hydrogen, methyl, ethyl, n-propyl, i-propyl, n-butyl, i-butyl, t-butyl, phenyl, naphthyl, biphenyl, terphenyl, anthryl, indenyl, phenanthryl, methoxy, ethoxy, propyloxy, butoxy, hydroxymethyl, hydroxyethyl, hydroxypropyl, hydroxybutyl, hydroxymethoxymethyl, hydroxymethoxyethyl, hydroxymethoxypropyl, hydroxymethoxybutyl, hydroxyethoxymethyl, hydroxyethoxyethyl, hydroxyethoxypropyl, hydroxyethoxybutyl, amino, nitro, cyano, or hydroxy.

3. The fluorene oxime ester compound of claim 1, wherein each $R_1$ is independently hydrogen or n-butyl;
$R_2$ is methyl; and
$R_3$ is methyl, n-butyl, or phenyl.

4. A photopolymerization initiator comprising the fluorene oxime ester compound of claim 1.

5. A photoresist composition comprising the fluorene oxime ester compound of claim 1.

6. The photoresist composition of claim 5, wherein the fluorene oxime ester compound of claim 1 is contained at a content of 0.01 to 10 weight % based on the photoresist composition.

7. A photoresist composition for a black matrix further comprising carbon black in addition to the photoresist composition of claim 5.

8. A photoresist composition for a color matrix further comprising a color pigment dispersion solution in addition to the photoresist composition of claim 5.

* * * * *